(12) United States Patent
Gross et al.

(10) Patent No.: US 10,881,858 B1
(45) Date of Patent: Jan. 5, 2021

(54) ELECTRICAL SUBSTANCE CLEARANCE FROM THE BRAIN

(71) Applicant: RAINBOW MEDICAL LTD., Herzeliyah (IL)

(72) Inventors: Yossi Gross, Moshav Mazor (IL); Alex Tendler, Haifa (IL)

(73) Assignee: RAINBOW MEDICAL LTD., Herzeliyah (IL)

(*) Notice: Subject to any disclaimer, the term of this patent is extended or adjusted under 35 U.S.C. 154(b) by 0 days.

(21) Appl. No.: 16/574,772

(22) Filed: Sep. 18, 2019

(51) Int. Cl.
*A61N 1/36* (2006.01)
*A61N 1/05* (2006.01)

(52) U.S. Cl.
CPC ....... *A61N 1/36082* (2013.01); *A61N 1/0504* (2013.01); *A61N 1/0534* (2013.01); *A61N 1/0536* (2013.01)

(58) Field of Classification Search
CPC .............. A61N 1/36082; A61N 1/0504; A61N 1/0536; A61N 1/0534
See application file for complete search history.

(56) References Cited

U.S. PATENT DOCUMENTS

| | | |
|---|---|---|
| 4,044,774 A | 8/1977 | Corbin et al. |
| 4,503,863 A | 3/1985 | Katims |
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |
| 5,792,100 A | 8/1998 | Shantha |
| 5,911,223 A | 6/1999 | Weaver et al. |
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |

(Continued)

FOREIGN PATENT DOCUMENTS

| | | |
|---|---|---|
| WO | 94/05369 | 3/1994 |
| WO | 01/52931 | 7/2001 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Amanda K Hulbert
*Assistant Examiner* — Natasha Patel
(74) *Attorney, Agent, or Firm* — Sughrue Mion, PLLC

(57) ABSTRACT

Apparatus is provided that includes an extracranial electrode, configured to be placed outside and in electrical contact with a skull of a subject identified as at risk of or suffering from a disease; and a cerebrospinal fluid (CSF) electrode, configured to be implanted in a ventricular system of a brain of the subject. Control circuitry is configured to drive the extracranial and the CSF electrodes to clear a substance from brain parenchyma of the subject into the ventricular system of the brain. Other embodiments are also described.

19 Claims, 4 Drawing Sheets

(56) References Cited

U.S. PATENT DOCUMENTS

| | | |
|---|---|---|
| 6,941,172 B2 | 9/2005 | Nachum |
| 6,997,941 B2 | 2/2006 | Sharkey et al. |
| 7,013,177 B1 | 3/2006 | Whitehurst et al. |
| 7,120,489 B2 | 10/2006 | Shalev et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,818,063 B2 | 10/2010 | Wallace et al. |
| 7,831,306 B2 | 11/2010 | Finch et al. |
| 7,860,569 B2 | 12/2010 | Solberg et al. |
| 8,060,207 B2 | 11/2011 | Wallace et al. |
| 8,103,350 B2 | 1/2012 | Wallace et al. |
| 8,190,248 B2 | 5/2012 | Besio et al. |
| 8,353,853 B1 | 1/2013 | Kyle et al. |
| 8,457,761 B2 | 6/2013 | Wariar |
| 8,577,469 B2 | 11/2013 | Gross |
| 8,676,348 B2 | 3/2014 | Gross |
| 8,731,674 B2 | 5/2014 | Wallace et al. |
| 9,616,221 B2 | 4/2017 | Gross |
| 9,724,513 B2 | 8/2017 | Lane et al. |
| 9,724,515 B2 | 8/2017 | Fostick et al. |
| 9,731,122 B2 | 8/2017 | Gross |
| 10,398,884 B2 | 9/2019 | Lad et al. |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0233202 A1 | 10/2007 | Wallace et al. |
| 2007/0255338 A1 | 11/2007 | Wahlstrand |
| 2008/0009927 A1 | 1/2008 | Vilims |
| 2008/0033503 A1 | 2/2008 | Fowler et al. |
| 2008/0119907 A1 | 5/2008 | Stahmann |
| 2008/0260542 A1 | 10/2008 | Nishikawa et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0160638 A1 | 6/2011 | Mauge et al. |
| 2011/0160797 A1 | 6/2011 | Makous et al. |
| 2012/0053659 A1 | 3/2012 | Molnar et al. |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2013/0289385 A1 | 10/2013 | Lozano et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0331970 A1 | 11/2016 | Lozano |
| 2017/0007823 A1 | 1/2017 | Gross |
| 2017/0056642 A1 | 3/2017 | Moffitt et al. |
| 2017/0105927 A1 * | 4/2017 | Thorne ............... A61K 9/0004 |
| 2017/0120053 A1 | 5/2017 | Fostick et al. |
| 2017/0182317 A1 | 6/2017 | Gross et al. |
| 2017/0296821 A1 | 10/2017 | Fostick et al. |
| 2018/0071523 A1 | 3/2018 | Gross et al. |
| 2018/0193646 A1 * | 7/2018 | Fostick ............. A61N 1/36082 |
| 2018/0318575 A1 * | 11/2018 | Gross ..................... A61N 1/205 |
| 2019/0282807 A1 | 9/2019 | Tendler et al. |
| 2020/0170509 A1 * | 6/2020 | Eide ..................... A61K 51/048 |

FOREIGN PATENT DOCUMENTS

| | | |
|---|---|---|
| WO | 01/85027 | 11/2001 |
| WO | 2001/085094 | 11/2001 |
| WO | 2006/090397 | 8/2006 |
| WO | 2008/007369 | 1/2008 |
| WO | 2017/006327 | 1/2017 |
| WO | 2017/072769 | 5/2017 |
| WO | 2017/115351 | 7/2017 |
| WO | 2018/051338 | 3/2018 |
| WO | 2019/175879 A1 | 9/2019 |

OTHER PUBLICATIONS

De La Tone JC, "Vascular Basis of Alzheimer's Pathogensis," Ann NY Acad Sci. 977:196-215 (Nov. 2002).

Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

U.S. Appl. No. 62/642,663, filed Mar. 14, 2018.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

Notice of Allowance dated Jul. 24, 2013, which issued during the prosecution of U.S. Appl. No. 12/373,306.

An Office Action dated Apr. 11, 2013, which issued during the prosecution of U.S. Appl. No. 13/663,757.

Notice of Allowance dated Oct. 28, 2013, which issued during the prosecution of U.S. Appl. No. 13/663,757.

Elixmann IM et al., "In-vitro evaluation of a drainage catheter with integrated bioimpedance electrodes to determine ventricular size," Biomed Tech 2013; 58 (Suppl. 1) Sep. 2013 (2 pages total).

An Office Action dated Aug. 31, 2015, which issued during the prosecution of U.S. Appl. No. 13/872,794.

An Applicant Initiated Interview Summary dated Dec. 14, 2015, which issued during the prosecution of U.S. Appl. No. 13/872,794.

An Office Action dated Feb. 3, 2016, which issued during the prosecution of U.S. Appl. No. 13/872,794.

Notice of Allowance dated Dec. 9, 2016, which issued during the prosecution of U.S. Appl. No. 14/794,739.

(56) References Cited

OTHER PUBLICATIONS

An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)-ATPase by an Oscillating Electric Field," The Journal of Biological Chemistry, vol. 265. No. 13, May 5, 1990. (pp. 7260-7267).
Robert F. Service . . . "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
An Office Action dated Jul. 10, 2019, which issued during the prosecution of U.S. Appl. No. 15/864,065.
An International Search Report and a Written Opinion both dated May 23, 2019, which issued during the prosecution of Applicant's PCT/IL2019/050284.
An Office Action dated Mar. 25, 2019, which issued during the prosecution of U.S. Appl. No. 15/742,245.
Borlase NM, "The thalamus in Parkinson's Disease," Department of Psychology, University of Canterbury, 2012.
Fernandes J, "Protein May Prevent Neuron Death in Huntington's Patients, Study Finds," huntingtonsdiseasenews.com, Jan. 19, 2017.
Lee H-J, "Extracellular αsynuclein a novel and crucial factor in Lewy body diseases," Nat. Rev. Neurol. 10, 92-98 (Feb. 2014); published online Jan. 28, 2014.
Starr PA et al., "Parkinson's Disease FAQ—Deep Brain Stimulation for Parkinson's Disease," UCSF Apr. 19, 2017.
Perez RG et al., "A Role for Alpha-Synuclein in the Regulation of Dopamine Biosynthesis," The Journal of Neuroscience, Apr. 15, 2002, 22(8):3090-3099.
Breydo L et al., "α-Synuclein misfolding and Parkinson's disease," Biochimica et Biophysica Acta 1822 (2012) 261-285 (Available online Oct. 12, 2011).
Deleidi M et al., "Protein Clearance Mechanisms of Alpha-Synuclein and Amyloid-Beta in Lewy Body Disorders," International Journal of Alzheimer's Disease, vol. 2012.
Xie L et al., "Sleep Drives Metabolite Clearance from the Adult Brain," Science. Oct. 18, 2013; 342(6156).
Valdinocci D et al., "Potential Modes of Intercellular α-Synuclein Transmission," International Journal of Molecular Sciences, Feb. 22, 2017.
U.S. Appl. No. 62/500,747, filed May 3, 2017.
An Office Action dated Jul. 29, 2019, which issued during the prosecution of U.S. Appl. No. 15/618,325.
Sawyer, P N et al. "Measurement of streaming potentials of mammalian blood vessels, aorta and vena cava, in vivo." Biophysical journal vol. 6,5 (1966): 641-51. doi:10.1016/50006-3495(66)86683-3, https://www.ncbi.nlm.nih.gov/pmc/articles/PMC1368020/, viewed on Jul. 22, 2019.
An Office Action dated Nov. 29, 2019, which issued during the prosecution of U.S. Appl. No. 15/969,411.
An Office Action dated Jan. 7, 2020, which issued during the prosecution of U.S. Appl. No. 15/618,325.
An Office Action dated Jan. 7, 2020, which issued during the prosecution of European Patent Application No. 16741703.9.
Office Action dated Nov. 20, 2020, which issued during the prosecution of U.S. Appl. No. 16/353,407.

\* cited by examiner

ELECTRICAL SUBSTANCE CLEARANCE FROM THE BRAIN

FIELD OF THE APPLICATION

The present invention relates generally to treatment and prevention of Alzheimer's disease and/or cerebral amyloid angiopathy (CAA), and specifically to electrical techniques for treating, preventing, or slowing the progression of Alzheimer's disease and/or CAA.

BACKGROUND OF THE APPLICATION

Alzheimer's disease is a chronic neurodegenerative disease that causes dementia. Accumulation of substances such as amyloid beta and/or tau protein in the brain is widely believed to contribute to the development of Alzheimer's disease.

US Patent Application Publication 2014/0324128 to Gross, which is assigned to the assignee of the present application and is incorporated herein by reference, describes apparatus for driving fluid between first and second anatomical sites of a subject. The apparatus comprises (1) a first electrode, configured to be coupled to the first anatomical site of the subject; (2) a second electrode, configured to be coupled to the second anatomical site of the subject; and (3) a control unit, configured to (i) detect a pressure difference between the first and second anatomical sites, and (ii) in response to the detected pressure difference, drive fluid between the first and second anatomical sites by applying a treatment voltage between the first and second electrodes. Other embodiments are also described.

PCT Publication WO 2017/072769 to Fostick et al., which is assigned to the assignee of the present application and is incorporated herein by reference, describes a system that includes a parenchymal electrode, configured to be implanted in brain parenchyma of a subject identified as at risk of or suffering from a disease; and a cerebrospinal fluid (CSF) electrode, configured to be implanted in a CSF-filled space of a brain of the subject, the CSF-filled space selected from the group consisting of: a ventricular system and a subarachnoid space. Control circuitry is configured to drive the parenchymal electrode and the CSF electrode to clear a substance from the brain parenchyma (50) into the CSF-filled space of the brain. Other embodiments are also described.

SUMMARY OF THE APPLICATION

Some embodiments of the present invention provide techniques for treating Alzheimer's disease and/or cerebral amyloid angiopathy (CAA). In some applications of the present invention, an extracranial electrode is placed (e.g., implanted) outside and in electrical contact with the skull, and a cerebrospinal fluid (CSF) electrode is implanted in a ventricular system of the brain. Control circuitry is activated to drive the extracranial and the CSF electrodes to clear a substance, such as amyloid beta and/or tau protein, from brain parenchyma either into the ventricular system of the brain or into the subarachnoid space and/or dural sinuses of the brain.

There is therefore provided, in accordance with an Inventive Concept 1 of the present invention, apparatus including:

an extracranial electrode, configured to be placed outside and in electrical contact with a skull of a subject identified as at risk of or suffering from a disease;

a cerebrospinal fluid (CSF) electrode, configured to be implanted in a ventricular system of a brain of the subject; and control circuitry, configured to drive the extracranial and the CSF electrodes to clear a substance from brain parenchyma of the subject into the ventricular system of the brain.

Inventive Concept 2. The apparatus according to Inventive Concept 1, wherein the extracranial electrode is configured to be implanted under skin of a head of the subject.

Inventive Concept 3. The apparatus according to Inventive Concept 1, wherein the extracranial electrode is configured to be placed on skin of a head of the subject.

Inventive Concept 4. The apparatus according to Inventive Concept 1, wherein the control circuitry is configured to be implanted under skin of the subject.

Inventive Concept 5. The apparatus according to Inventive Concept 1, wherein the disease is Alzheimer's disease, and wherein the extracranial electrode is configured to placed outside and in electrical contact with the skull of the subject identified as at risk of or suffering from Alzheimer's disease.

Inventive Concept 6. The apparatus according to Inventive Concept 1, wherein the disease is cerebral amyloid angiopathy (CAA), and wherein the extracranial electrode is configured to placed outside and in electrical contact with the skull of the subject identified as at risk of or suffering from CAA.

Inventive Concept 7. The apparatus according to Inventive Concept 1, wherein the substance includes amyloid beta, and wherein the control circuitry is configured to drive the extracranial and the CSF electrodes to clear the amyloid beta from the brain parenchyma into the ventricular system of the brain.

Inventive Concept 8. The apparatus according to Inventive Concept 1, wherein the substance includes tau protein, and wherein the control circuitry is configured to drive the extracranial and the CSF electrodes to clear the tau protein from the brain parenchyma into the ventricular system of the brain.

Inventive Concept 9. The apparatus according to Inventive Concept 1, wherein the apparatus includes a plurality of extracranial electrodes, and wherein the control circuitry is configured to drive a first average charge between (a) one or more extracranial electrodes of a first subset of the extracranial electrodes and (b) the CSF electrode over a 24-hour period of time, and a second average charge between (a) one or more extracranial electrodes of a second subset of the extracranial electrodes and (b) the CSF electrode over the 24-hour period of time, the first average charge greater than the second average charge.

Inventive Concept 10. The apparatus according to Inventive Concept 1, wherein the control circuitry is configured to configure the extracranial electrode to be an anode, and the CSF electrode to be a cathode.

Inventive Concept 11. The apparatus according to Inventive Concept 1, wherein the control circuitry is configured to configure the extracranial electrode to be a cathode, and the CSF electrode to be an anode.

Inventive Concept 12. The apparatus according to Inventive Concept 1, wherein the control circuitry is configured to drive the extracranial and the CSF electrodes to clear the substance by applying a non-excitatory current between the extracranial and the CSF electrodes.

Inventive Concept 13. The apparatus according to Inventive Concept 1, wherein the control circuitry is configured to drive the extracranial and the CSF electrodes to clear the substance by applying direct current between the extracranial and the CSF electrodes.

Inventive Concept 14. The apparatus according to Inventive Concept 13, wherein the control circuitry is configured to apply the direct current with an average amplitude of between 1 and 5 mA.

Inventive Concept 15. The apparatus according to Inventive Concept 13, wherein the control circuitry is configured to apply the direct current with an average amplitude of less than 1.2 V.

Inventive Concept 16. The apparatus according to Inventive Concept 13, wherein the control circuitry is configured to apply the direct current as a series of pulses.

Inventive Concept 17. The apparatus according to Inventive Concept 16, wherein the control circuitry is configured to apply the direct current as the series of pulses having an average pulse duration of between 100 milliseconds and 300 seconds.

Inventive Concept 18. The apparatus according to Inventive Concept 16, wherein the control circuitry is configured to apply the direct current as the series of pulses with a duty cycle of between 1 and 50%.

There is further provided, in accordance with an Inventive Concept 19 of the present invention, a method including:

placing an extracranial electrode outside and in electrical contact with a skull of a subject identified as at risk of or suffering from a disease;

implanting a cerebrospinal fluid (CSF) electrode in a ventricular system of a brain of the subject; and activating control circuitry to drive the extracranial and the CSF electrodes to clear a substance from brain parenchyma into the ventricular system of the brain.

Inventive Concept 20. The method according to Inventive Concept 19, wherein placing the extracranial electrode includes implanting the extracranial electrode under skin of a head of the subject.

Inventive Concept 21. The method according to Inventive Concept 19, wherein placing the extracranial electrode includes placing the extracranial electrode on skin of a head of the subject.

Inventive Concept 22. The method according to Inventive Concept 19, further including implanting the control circuitry under skin of the subject.

Inventive Concept 23. The method according to Inventive Concept 19, wherein the disease is Alzheimer's disease, and wherein placing the extracranial electrode includes placing the extracranial electrode outside and in electrical contact with the skull of the subject identified as at risk of or suffering from Alzheimer's disease.

Inventive Concept 24. The method according to Inventive Concept 19, wherein the disease is cerebral amyloid angiopathy (CAA), and wherein placing the extracranial electrode includes placing the extracranial electrode outside and in electrical contact with the skull of the subject identified as at risk of or suffering from CAA.

Inventive Concept 25. The method according to Inventive Concept 19, wherein the substance includes amyloid beta, and wherein activating the control circuitry includes activating the control circuitry to drive the extracranial and the CSF electrodes to clear the amyloid beta from the brain parenchyma into the ventricular system of the brain.

Inventive Concept 26. The method according to Inventive Concept 19, wherein the substance includes tau protein, and wherein activating the control circuitry includes activating the control circuitry to drive the extracranial and the CSF electrodes to clear the tau protein from the brain parenchyma into the ventricular system of the brain.

Inventive Concept 27. The method according to Inventive Concept 19, wherein placing the extracranial electrode includes placing the extracranial electrode such that an area of build-up of the substance is between the extracranial electrode and an area of the ventricular system of the brain nearest the area of build-up.

Inventive Concept 28. The method according to Inventive Concept 27, wherein placing the extracranial electrode includes identifying the area of build-up of the substance in the brain parenchyma before placing the extracranial electrode.

Inventive Concept 29. The method according to Inventive Concept 28, wherein identifying the area of build-up includes performing imaging of the brain.

Inventive Concept 30. The method according to Inventive Concept 29, wherein performing the imaging includes performing functional MRI (fMRI) imaging of the brain.

Inventive Concept 31. The method according to Inventive Concept 27, wherein placing the extracranial electrode includes placing a plurality of extracranial electrodes, such that a first subset of the plurality of extracranial electrodes are located such that one or more respective areas of build-up of the substance in the brain parenchyma are between one or more of the extracranial electrodes and respective areas of the ventricular system.

Inventive Concept 32. The method according to Inventive Concept 31, wherein activating the control circuitry to clear the substance from the brain parenchyma includes activating the control circuitry to drive a first average charge between the one or more extracranial electrodes of the first subset and the CSF electrode over a 24-hour period of time, and a second average charge between (a) one or more extracranial electrodes of a second subset of the one or more extracranial electrodes and (b) the CSF electrode over the 24-hour period of time, the first average charge greater than the second average charge, and the first and the second subsets not including any extracranial electrodes common to both subsets.

Inventive Concept 33. The method according to Inventive Concept 19, wherein placing the extracranial electrode includes placing a plurality of extracranial electrodes, and wherein the method further includes, after placing the plurality of extracranial electrodes:

identifying one or more areas of build-up of the substance in the parenchyma between the extracranial electrodes and respective areas of the ventricular system of the brain nearest the areas of build-up; and identifying a first subset of the one or more extracranial electrodes as located such that one or more of the areas of build-up of the substance in brain parenchyma are between the one or more extracranial electrodes and the respective areas of the ventricular system.

Inventive Concept 34. The method according to Inventive Concept 33, wherein activating the control circuitry to clear the substance from the brain parenchyma includes activating the control circuitry to drive a first average charge between the one or more extracranial electrodes of the first subset and the CSF electrode over a 24-hour period of time, and a second average charge between (a) the one or more extracranial electrodes of a second subset of the one or more extracranial electrodes and (b) the CSF electrode over the 24-hour period of time, the first average charge greater than the second average charge, and the first and the second subsets not including any extracranial electrodes common to both subsets.

Inventive Concept 35. The method according to Inventive Concept 33, wherein identifying the one or more areas of build-up includes performing imaging of the brain.

Inventive Concept 36. The method according to Inventive Concept 19, wherein the extracranial electrode includes a plurality of extracranial electrodes, and wherein placing the extracranial electrode includes placing a two-dimensional arrangement of the extracranial electrodes around a portion of the skull.

Inventive Concept 37. The method according to Inventive Concept 19, wherein activating the control circuitry includes activating the control circuitry to configure the extracranial electrode to be an anode, and the CSF electrode to be a cathode.

Inventive Concept 38. The method according to Inventive Concept 19, wherein activating the control circuitry includes activating the control circuitry to configure the extracranial electrode to be a cathode, and the CSF electrode to be an anode.

Inventive Concept 39. The method according to Inventive Concept 19, wherein activating the control circuitry to drive the extracranial and the CSF electrodes includes activating the control circuitry to drive the extracranial and the CSF electrodes to clear the substance by applying a non-excitatory current between the extracranial and the CSF electrodes.

Inventive Concept 40. The method according to Inventive Concept 19, wherein activating the control circuitry to drive the extracranial and the CSF electrodes includes activating the control circuitry to drive the extracranial and the CSF electrodes to clear the substance by applying direct current between the extracranial and the CSF electrodes.

Inventive Concept 41. The method according to Inventive Concept 40, wherein activating the control circuitry to apply the direct current includes activating the control circuitry to apply the direct current with an average amplitude of between 1 and 5 mA.

Inventive Concept 42. The method according to Inventive Concept 40, wherein activating the control circuitry to apply the direct current includes activating the control circuitry to apply the direct current with an average amplitude of less than 1.2 V.

Inventive Concept 43. The method according to Inventive Concept 40, wherein activating the control circuitry to apply the direct current includes activating the control circuitry to apply the direct current as a series of pulses.

Inventive Concept 44. The method according to Inventive Concept 43, wherein activating the control circuitry to apply the direct current as the series of pulses includes activating the control circuitry to apply the direct current as the series of pulses having an average pulse duration of between 100 milliseconds and 300 seconds.

Inventive Concept 45. The method according to Inventive Concept 43, wherein activating the control circuitry to apply the direct current as the series of pulses includes activating the control circuitry to apply the direct current as the series of pulses with a duty cycle of between 1% and 50%.

There is still further provided, in accordance with an Inventive Concept 46 of the present invention, apparatus including:

a two-dimensional arrangement of extracranial electrodes, configured to be placed outside and in electrical contact with a skull of a subject identified as at risk of or suffering from a disease;

a cerebrospinal fluid (CSF) electrode, configured to be implanted in a ventricular system of a brain of the subject; and control circuitry, configured to drive the extracranial and the CSF electrodes to clear a substance from brain parenchyma of the subject into at least one region of the brain selected from the group consisting of: a subarachnoid space of the brain and dural sinuses of the brain.

Inventive Concept 47. The apparatus according to Inventive Concept 46, wherein the control circuitry is configured to drive the extracranial and the CSF electrodes to clear the substance from the brain parenchyma into at least the subarachnoid space.

Inventive Concept 48. The apparatus according to Inventive Concept 46, wherein the control circuitry is configured to drive the extracranial and the CSF electrodes to clear the substance from the brain parenchyma into at least the dural sinuses.

Inventive Concept 49. The apparatus according to Inventive Concept 46, wherein the extracranial electrodes are configured to be implanted under skin of a head of the subject.

Inventive Concept 50. The apparatus according to Inventive Concept 46, wherein the extracranial electrodes are configured to be placed on skin of a head of the subject.

Inventive Concept 51. The apparatus according to Inventive Concept 46, wherein the control circuitry is configured to be implanted under skin of the subject.

Inventive Concept 52. The apparatus according to Inventive Concept 46, wherein the disease is Alzheimer's disease, and wherein the two-dimensional arrangement of extracranial electrodes is configured to placed outside and in electrical contact with the skull of the subject identified as at risk of or suffering from Alzheimer's disease.

Inventive Concept 53. The apparatus according to Inventive Concept 46, wherein the disease is cerebral amyloid angiopathy (CAA), and wherein the two-dimensional arrangement of extracranial electrodes is configured to placed outside and in electrical contact with the skull of the subject identified as at risk of or suffering from CAA.

Inventive Concept 54. The apparatus according to Inventive Concept 46, wherein the substance includes amyloid beta, and wherein the control circuitry is configured to drive the extracranial and the CSF electrodes to clear the amyloid beta from the brain parenchyma into the at least one region of the brain.

Inventive Concept 55. The apparatus according to Inventive Concept 46, wherein the substance includes tau protein, and wherein the control circuitry is configured to drive the extracranial and the CSF electrodes to clear the tau protein from the brain parenchyma into the at least one region of the brain.

Inventive Concept 56. The apparatus according to Inventive Concept 46, wherein the two-dimensional arrangement includes at least a 2×3 arrangement of the extracranial electrodes.

Inventive Concept 57. The apparatus according to Inventive Concept 56, wherein the two-dimensional arrangement includes at least a 4×4 arrangement of the extracranial electrodes.

Inventive Concept 58. The apparatus according to Inventive Concept 46, wherein the control circuitry is configured to drive a first average charge between (a) one or more extracranial electrodes of a first subset of the extracranial electrodes and (b) the CSF electrode over a 24-hour period of time, and a second average charge between (a) one or more extracranial electrodes of a second subset of the extracranial electrodes and (b) the CSF electrode over the 24-hour period of time, the first average charge greater than the second average charge.

Inventive Concept 59. The apparatus according to Inventive Concept 46, wherein the control circuitry is configured to configure the extracranial electrodes to be anodes, and the CSF electrode to be a cathode.

Inventive Concept 60. The apparatus according to Inventive Concept 46, wherein the control circuitry is configured to configure the extracranial electrodes to be cathodes, and the CSF electrode to be an anode.

Inventive Concept 61. The apparatus according to Inventive Concept 46, wherein the control circuitry is configured to drive the extracranial and the CSF electrodes to clear the substance by applying a non-excitatory current between the extracranial and the CSF electrodes.

Inventive Concept 62. The apparatus according to Inventive Concept 46, wherein the control circuitry is configured to drive the extracranial and the CSF electrodes to clear the substance by applying direct current between the extracranial and the CSF electrodes.

Inventive Concept 63. The apparatus according to Inventive Concept 62, wherein the control circuitry is configured to apply the direct current with an average amplitude of between 1 and 5 mA.

Inventive Concept 64. The apparatus according to Inventive Concept 62, wherein the control circuitry is configured to apply the direct current with an average amplitude of less than 1.2 V.

Inventive Concept 65. The apparatus according to Inventive Concept 62, wherein the control circuitry is configured to apply the direct current as a series of pulses.

Inventive Concept 66. The apparatus according to Inventive Concept 65, wherein the control circuitry is configured to apply the direct current as the series of pulses having an average pulse duration of between 100 milliseconds and 300 seconds.

Inventive Concept 67. The apparatus according to Inventive Concept 65, wherein the control circuitry is configured to apply the direct current as the series of pulses with a duty cycle of between 1% and 50%.

There is additionally provided, in accordance with an Inventive Concept 68 of the present invention, a method including:

placing a two-dimensional arrangement of extracranial electrodes outside and in electrical contact with a skull of a subject identified as at risk of or suffering from a disease;

implanting a cerebrospinal fluid (CSF) electrode in a ventricular system of a brain of the subject; and activating control circuitry to drive the extracranial and the CSF electrodes to clear a substance from brain parenchyma into at least one region of the brain selected from the group consisting of: a subarachnoid space of the brain and dural sinuses of the brain.

Inventive Concept 69. The method according to Inventive Concept 68, wherein activating the control circuitry includes activating the control circuitry to drive the extracranial and the CSF electrodes to clear the substance from the brain parenchyma into at least the subarachnoid space.

Inventive Concept 70. The method according to Inventive Concept 68, wherein activating the control circuitry includes activating the control circuitry to clear the substance from the brain parenchyma into at least the dural sinuses.

Inventive Concept 71. The method according to Inventive Concept 68, wherein placing the two-dimensional arrangement of extracranial electrodes includes implanting the extracranial electrodes under skin of a head of the subject.

Inventive Concept 72. The method according to Inventive Concept 68, wherein placing the two-dimensional arrangement of extracranial electrodes includes placing the extracranial electrodes on skin of a head of the subject.

Inventive Concept 73. The method according to Inventive Concept 68, further including implanting the control circuitry under skin of the subject.

Inventive Concept 74. The method according to Inventive Concept 68, wherein the disease is Alzheimer's disease, and wherein placing the two-dimensional arrangement of extracranial electrodes includes placing the two-dimensional arrangement of extracranial electrodes outside and in electrical contact with the skull of the subject identified as at risk of or suffering from Alzheimer's disease.

Inventive Concept 75. The method according to Inventive Concept 68, wherein the disease is cerebral amyloid angiopathy (CAA), and wherein placing the two-dimensional arrangement of extracranial electrodes includes placing the two-dimensional arrangement of extracranial electrode outsides and in electrical contact with the skull of the subject identified as at risk of or suffering from CAA.

Inventive Concept 76. The method according to Inventive Concept 68, wherein the substance includes amyloid beta, and wherein activating the control circuitry includes activating the control circuitry to drive the extracranial and the CSF electrodes to clear the amyloid beta from the brain parenchyma into the at least one region of the brain.

Inventive Concept 77. The method according to Inventive Concept 68, wherein the substance includes tau protein, and wherein activating the control circuitry includes activating the control circuitry to drive the extracranial and the CSF electrodes to clear the tau protein from the brain parenchyma into the at least one region of the brain.

Inventive Concept 78. The method according to Inventive Concept 68, wherein placing the two-dimensional arrangement of extracranial electrodes includes placing the two-dimensional arrangement of extracranial electrodes such that an area of build-up of the substance is between the two-dimensional arrangement of extracranial electrodes and an area of the ventricular system of the brain nearest the area of build-up.

Inventive Concept 79. The method according to Inventive Concept 78, wherein placing the two-dimensional arrangement of extracranial electrodes includes identifying the area of build-up of the substance in the brain parenchyma before placing the two-dimensional arrangement of extracranial electrodes.

Inventive Concept 80. The method according to Inventive Concept 79, wherein identifying the area of build-up includes performing imaging of the brain.

Inventive Concept 81. The method according to Inventive Concept 80, wherein performing the imaging includes performing functional MRI (fMRI) imaging of the brain.

Inventive Concept 82. The method according to Inventive Concept 78, wherein placing the two-dimensional arrangement of extracranial electrodes includes placing the two-dimensional arrangement of extracranial electrodes such that a first subset of the one or more extracranial electrodes are located such that one or more respective areas of build-up of the substance in the brain parenchyma are between the one or more extracranial electrodes and respective areas of the ventricular system.

Inventive Concept 83. The method according to Inventive Concept 82, wherein activating the control circuitry to clear the substance from the brain parenchyma includes activating the control circuitry to drive a first average charge between the one or more extracranial electrodes of the first subset and the CSF electrode over a 24-hour period of time, and a second average charge between (a) one or more extracranial electrodes of a second subset of the one or more extracranial electrodes and (b) the CSF electrode over the 24-hour period of time, the first average charge greater than the second average charge, and the first and the second subsets not including any extracranial electrodes common to both subsets.

Inventive Concept 84. The method according to Inventive Concept 68, further including, after placing the two-dimensional arrangement of extracranial electrodes:
  identifying one or more areas of build-up of the substance in the parenchyma between the two-dimensional arrangement of extracranial electrodes and respective areas of the ventricular system of the brain nearest the areas of build-up; and
  identifying a first subset of the one or more extracranial electrodes as located such that one or more of the areas of build-up of the substance in brain parenchyma are between the one or more extracranial electrodes and the respective areas of the ventricular system.

Inventive Concept 85. The method according to Inventive Concept 84, wherein activating the control circuitry to clear the substance from the brain parenchyma includes activating the control circuitry to drive a first average charge between the one or more extracranial electrodes of the first subset and the CSF electrode over a 24-hour period of time, and a second average charge between (a) one or more extracranial electrodes of a second subset of the one or more extracranial electrodes and (b) the CSF electrode over the 24-hour period of time, the first average charge greater than the second average charge, and the first and the second subsets not including any extracranial electrodes common to both subsets.

Inventive Concept 86. The method according to Inventive Concept 84, wherein identifying the one or more areas of build-up includes performing imaging of the brain.

Inventive Concept 87. The method according to Inventive Concept 68, wherein activating the control circuitry includes activating the control circuitry to configure the extracranial electrodes to be anodes, and the CSF electrode to be a cathode.

Inventive Concept 88. The method according to Inventive Concept 68, wherein activating the control circuitry includes activating the control circuitry to configure the extracranial electrodes to be cathodes, and the CSF electrode to be an anode.

Inventive Concept 89. The method according to Inventive Concept 68, wherein activating the control circuitry to drive the extracranial and the CSF electrodes includes activating the control circuitry to drive the extracranial and the CSF electrodes to clear the substance by applying a non-excitatory current between the extracranial and the CSF electrodes.

Inventive Concept 90. The method according to Inventive Concept 68, wherein activating the control circuitry to drive the extracranial and the CSF electrodes includes activating the control circuitry to drive the extracranial and the CSF electrodes to clear the substance by applying direct current between the extracranial and the CSF electrodes.

Inventive Concept 91. The method according to Inventive Concept 90, wherein activating the control circuitry to apply the direct current includes activating the control circuitry to apply the direct current with an average amplitude of between 1 and 5 mA.

Inventive Concept 92. The method according to Inventive Concept 90, wherein activating the control circuitry to apply the direct current includes activating the control circuitry to apply the direct current with an average amplitude of less than 1.2 V.

Inventive Concept 93. The method according to Inventive Concept 90, wherein activating the control circuitry to apply the direct current includes activating the control circuitry to apply the direct current as a series of pulses.

Inventive Concept 94. The method according to Inventive Concept 93, wherein activating the control circuitry to apply the direct current as the series of pulses includes activating the control circuitry to apply the direct current as the series of pulses having an average pulse duration of between 100 milliseconds and 300 seconds.

Inventive Concept 95. The method according to Inventive Concept 93, wherein activating the control circuitry to apply the direct current as the series of pulses includes activating the control circuitry to apply the direct current as the series of pulses with a duty cycle of between 1% and 50%.

The present invention will be more fully understood from the following detailed description of embodiments thereof, taken together with the drawings, in which:

DETAILED DESCRIPTION OF APPLICATIONS

Figure 1A:
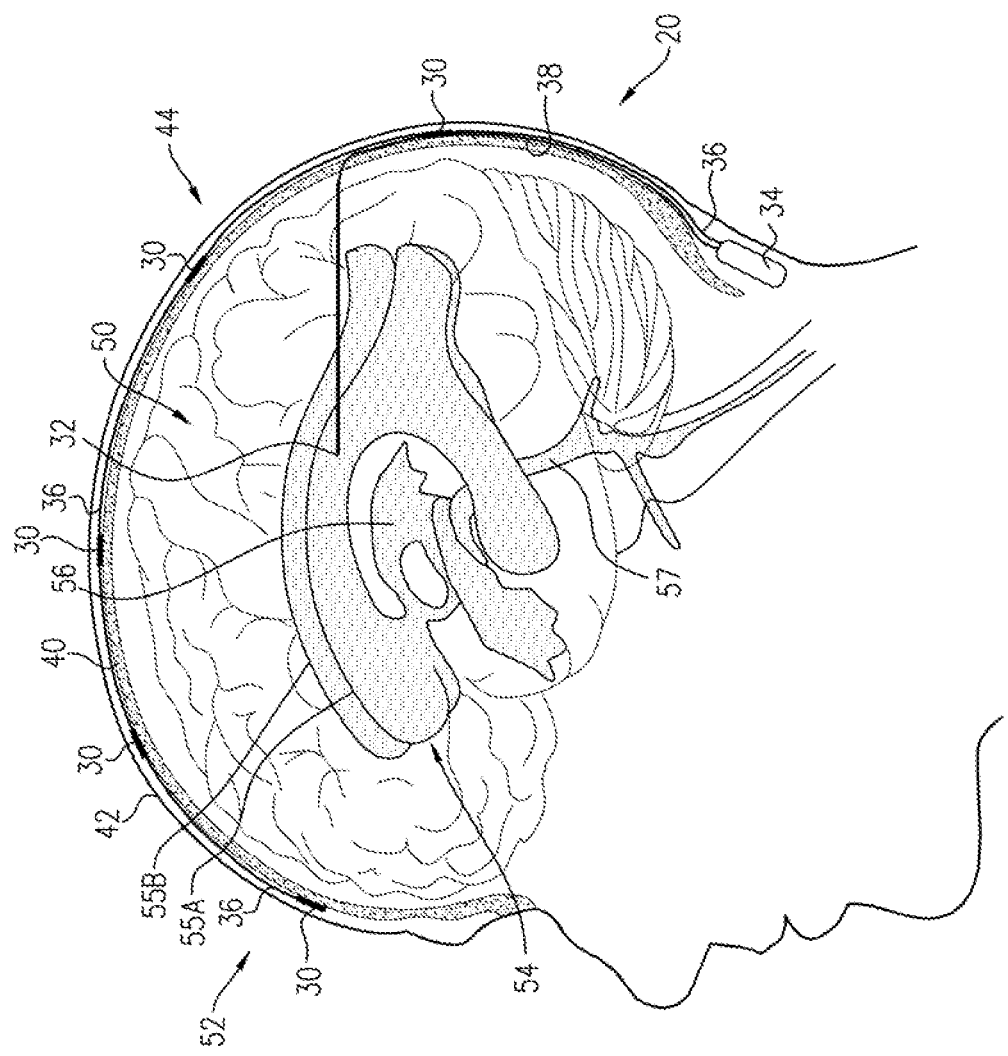
FIGS. 1A-C are schematic illustrations of a system for treating Alzheimer's disease, in accordance with respective applications of the present invention.
Figure 1B:
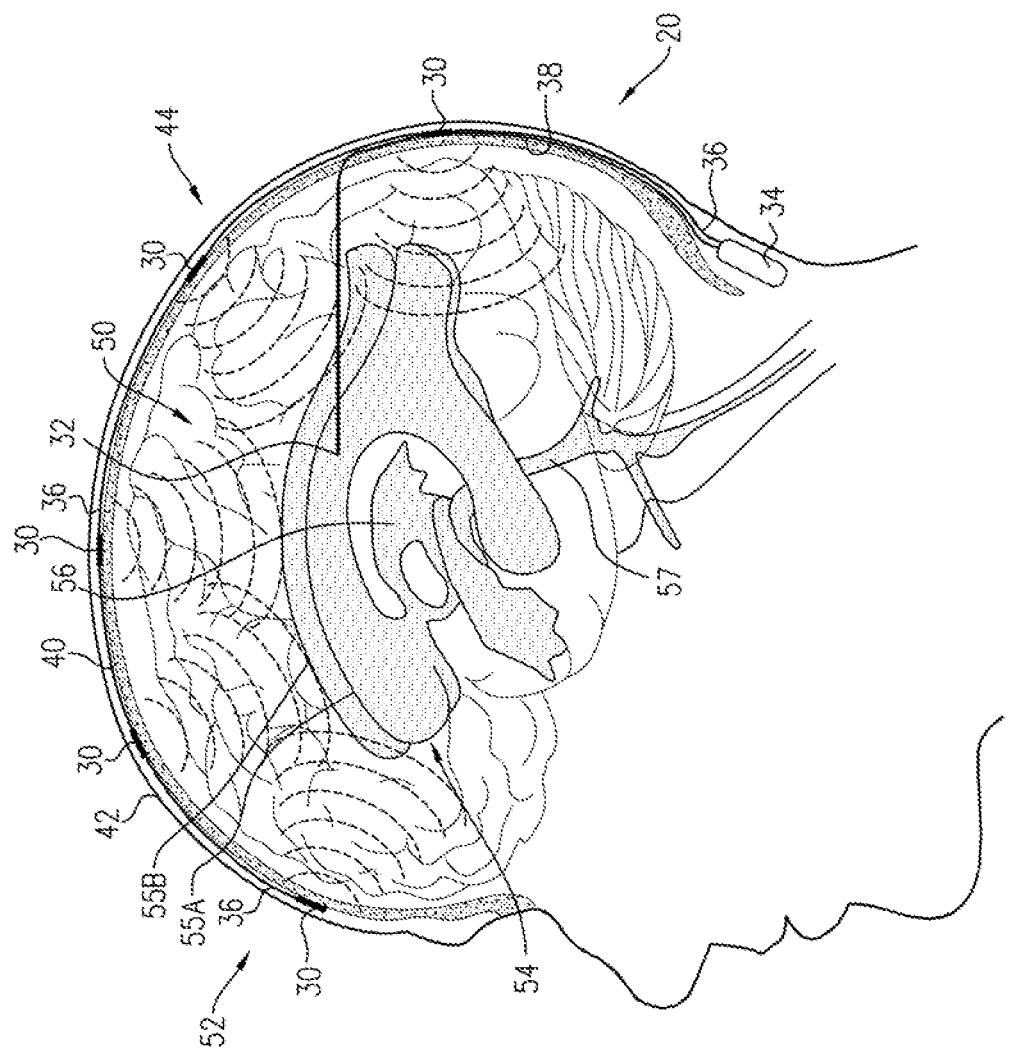
Figure 1C:
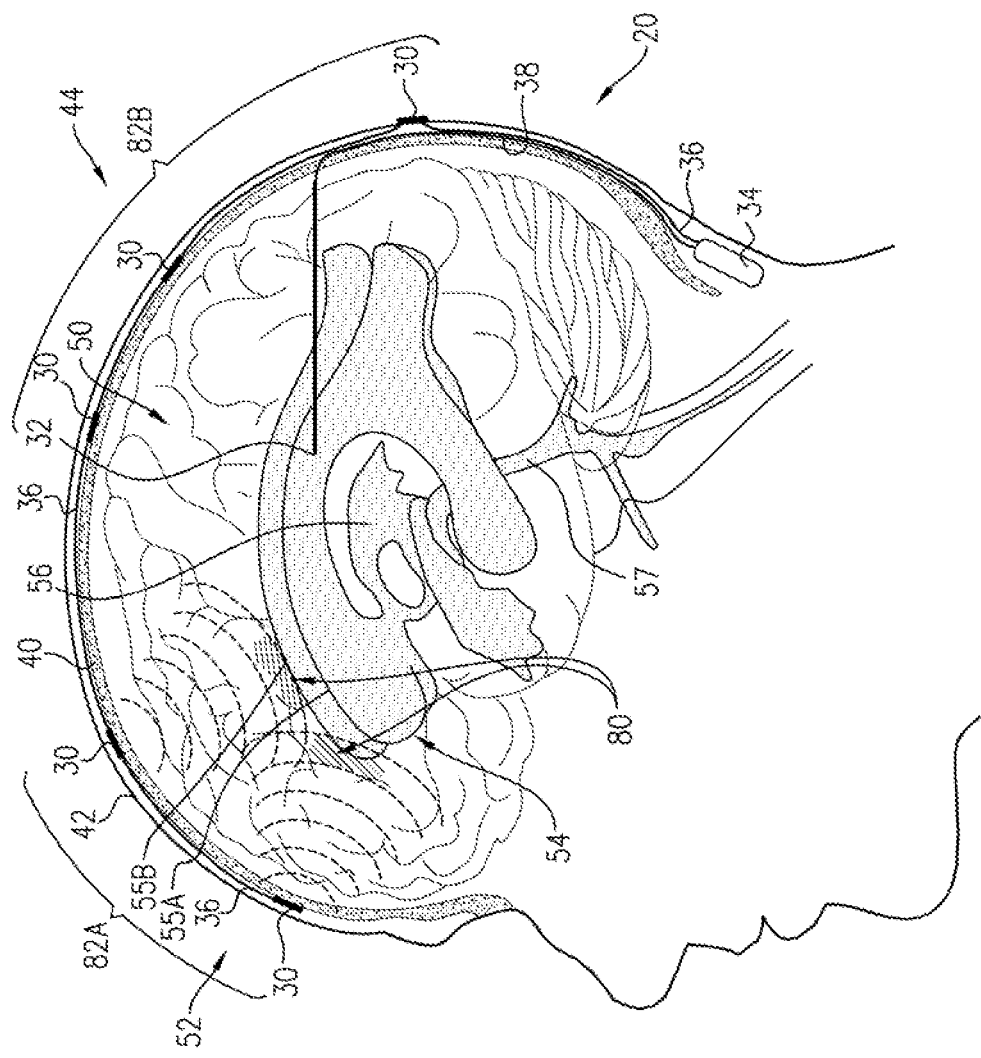

FIGS. 1A-C are schematic illustrations of a system for treating Alzheimer's disease and/or cerebral amyloid angiopathy (CAA), in accordance with respective applications of the present invention. System 20 comprises extracranial and cerebrospinal fluid (CSF) electrodes 30 and 32, and control circuitry 34, which is electrically coupled to extracranial and CSF electrodes 30 and 32, typically by extracranial and CSF electrode leads 36 and 38, respectively.

In some applications of the present invention, as shown for the three extracranial electrodes 30 illustrated in FIG. 1A, extracranial electrode 30 is placed outside and in electrical contact with a skull 40 of a subject identified as at risk of or suffering from Alzheimer's disease and/or from CAA. For some applications, extracranial electrode 30 is implanted under skin 42 of a head 44 of the subject, such as shown in FIGS. 1A-C. Alternatively, extracranial electrode 30 is placed on skin 42 of head 44 (i.e., on an external surface of skin 42, rather than under skin 42), as shown for the rightmost electrode 30 in FIG. 1C. CSF electrode 32 is implanted in a CSF-filled space of the brain, such as ventricular system 54 of a brain 52 of the subject or a subarachnoid space (e.g., cisterns of the subarachnoid space). For example, CSF electrode 32 may be implanted using techniques known for implanting hydrocephalus shunts, mutatis mutandis (e.g., via a bore through the back of skull 40). As used in the present application, including in the claims, ventricular system 54 includes and is limited to lateral ventricles 55 (left and right lateral ventricles 55A and 55B), a third ventricle 56, a fourth ventricle 57, a cerebral aqueduct, interventricular foramina, a median aperture, and left and right lateral apertures.

In some applications of the present invention, control circuitry 34 is activated to drive extracranial and CSF electrodes 30 and 32 to clear a substance from brain parenchyma 50 into the CSF-filled space, such as ventricular system 54. For some applications, the substance comprises amyloid beta, a tau protein, metal ions, and/or a waste substance. As used in the present application, including in the claims, clearing a substance from the brain parenchyma is to be understood as including clearing a portion of the substance, without clearing all of the substance. Typically, in order to clear the substance, control circuitry 34 applies a voltage or a current between extracranial and CSF electrodes 30 and 32 (i.e., control circuitry 34 regulates the voltage or the current).

In other applications of the present invention, control circuitry 34 is activated to drive extracranial and CSF electrodes 30 and 32 to clear the substance from brain parenchyma 50 into a subarachnoid space and/or dural sinuses of the brain. In contrast to the applications described immediately above in which the substance is cleared in a generally inward direction from brain parenchyma 50 to ventricular system 54, in the present applications the substance is cleared in a generally outward direction from brain parenchyma 50 to the subarachnoid space and dural sinuses, which are located outwardly from the parenchyma and nearer to skull 40. As is known in the biological arts, the dural sinuses (also known as the dural venous sinuses) are venous channels located between the endosteal and meningeal layers of dura mater in the brain. The dural sinuses receive blood from the cerebral veins, receive CSF from the subarachnoid space via arachnoid granulations, and mainly empty into the internal jugular vein. The superior sagittal sinus is one of the dural sinuses.

Typically, a healthcare worker, such as a physician, activates control circuitry 34 to provide the functions described herein. Activating the control unit may include configuring parameters and/or functions of the control circuitry (such as using a separate programmer or external controller), or activating the control unit to perform functions pre-programmed in the control circuitry. Control circuitry 34 typically comprises appropriate memory, processor(s), and hardware running software that is configured to provide the functionality of control circuitry described herein.

Current may flow generally through parenchymal tissue that is located between extracranial and CSF electrodes 30 and 32. Alternatively or additionally, at least a portion of the current may flow from extracranial electrode 30, through parenchymal tissue, to an area of the CSF-filled space (e.g., ventricular system 54) nearest extracranial electrode 30. The inventors have appreciated that because of the low electrical resistance of cerebrospinal fluid (CSF) in the CSF-filled space, such as ventricular system 54, the ventricles are to some extent a single entity electrically. Therefore, a large portion of the current flows to the nearest portion of ventricular system 54, even if CSF electrode 32 is implanted in a ventricle remote from extracranial electrode 30. For example, if an extracranial electrode 30 is placed over a right hemisphere of brain 52, most of the current may flow between the extracranial electrode 30 and an area of right ventricle 55B nearest the extracranial electrode, even though CSF electrode 32 is implanted in left lateral ventricle 55A.

For some applications, the voltage applied between the electrodes may clear the substance electrophoretically, because of a positive or negative charged interface between the surface of the particles of the substance and the surrounding brain tissue fluids. For these applications, the voltage applied between the electrodes causes a potential difference between brain parenchyma 50 and the CSF-filled space, such as ventricular system 54, which causes movement of the substance from brain parenchyma 50 to the CSF-filled space, such as ventricular system 54. Alternatively or additionally, for some applications, the voltage applied between the electrodes may clear the substance electroosmotically, because of a positive or negative charge of fluid in the parenchyma. For these applications, the voltage applied between the electrodes causes a potential difference between brain parenchyma 50 and the CSF-filled space, such as ventricular system 54, which causes increased flow from brain parenchyma 50 to the CSF-filled space, such as ventricular system 54, and thus increased transport of the substance from parenchyma 50 to the CSF-filled space, such as ventricular system 54.

For some applications, system 20 comprises a plurality of extracranial electrodes 30 and/or a plurality of CSF electrodes 32. Extracranial electrodes 30 may be placed over one or both hemispheres of brain 52, and/or at one or more than one location in each of the hemispheres. For some applications, such as shown in FIGS. 1A-C, system 20 comprises a plurality of extracranial electrodes 30 and exactly one CSF electrode 32. For example, the single CSF electrode 32 may be implanted in one of lateral ventricles 55 or third ventricle 56, which, as discussed above, are to a large degree in good electrical connectivity with the other ventricles. For other applications (configuration not shown), system 20 comprises (a) exactly two CSF electrodes 32, which are implanted in left and right lateral ventricles 55A and 55B, respectively, or (b) exactly three CSF electrodes 32, which are implanted in left and right lateral ventricles 55A and 55B and third ventricle 56, respectively.

For applications in which system 20 comprises a plurality of extracranial electrodes 30 and/or a plurality of CSF electrodes 32, system 20 may comprise a corresponding plurality of extracranial electrode leads 36 and/or a corresponding plurality of CSF electrode leads 38. Each of the leads may comprise separate electrical insulation, and/or a portion of the leads may be joined and share common electrical insulation, as shown in FIGS. 1A-C for extracranial electrode leads 36. Control circuitry 34 may be activated to independently drive extracranial electrodes 30, e.g., using separately circuitry; in other words, extracranial electrode leads 36 may be separately controllable or addressable by control circuitry 34. Alternatively, one or more of extracranial electrodes 30 may be shorted to one another, such that the control circuitry drives the shorted electrodes together. Control circuitry 34 may be activated to drive extracranial electrodes 30 simultaneously or at different times.

For some applications, the one or more extracranial electrodes 30 comprise respective exposed electrode surfaces having an average surface area of at least 4 mm2 (for example, 2×2 mm), no more than 100 mm2 (for example, 10×10 mm), and/or between 4 and 100 mm2.

As used in the present application, including the claims, "treating" includes both treating a subject already diagnosed with Alzheimer's disease and/or CAA (such as by delaying, slowing, or reversing progression of the disease, e.g., in a patient diagnosed at an early stage), as well as preventing the development of Alzheimer's disease and/or CAA in a subject not diagnosed with the disease and/or asymptomatic for the disease. For example, the techniques described herein may be used to prevent or delay the development of Alzheimer's disease and/or CAA in responsive to detection of an abnormal level of amyloid beta, such as using a blood test or a spinal tap.

For some applications, control circuitry 34 is configured to be implanted subcutaneously, such under skin 42 of head 44 of the subject if the housing containing the control circuitry is small, or elsewhere in the subject's body, such as in the upper chest, if the housing of the control circuitry is larger (e.g., includes batteries), with leads through the neck, or optionally in the head. For these applications, control circuitry 34 is typically driven by an external controller that is in wireless or wired communication with control circuitry 34. For some applications, the external controller is mounted on a bed of the subject (e.g., disposed within a mattress), and is configured to activate control circuitry 34 only at night, and/or only when the subject is sleeping. Such nighttime activation may to some degree mimic the natural timing of clearance of the substance (e.g., amyloid beta or tau protein) during sleep, during which the extracellular spaces are wider than during wakefulness, which allows more interstitial fluid (ISF) flow within the brain. For other applications, control circuitry 34 is configured to be disposed externally to the subject.

For some applications, control circuitry 34 is activated to drive extracranial and CSF electrodes 30 and 32 to clear the substance by applying a non-excitatory current between extracranial and CSF electrodes 30 and 32, i.e., the current does not cause propagation of action potentials. Thus, in these applications, control circuitry 34 is activated to set parameters of the current such that the current does not affect, or only minimally affects, neuronal activity. Alternatively, the applied current does excite brain tissue, such as to a small extent.

For some applications, control circuitry 34 is activated to drive extracranial and CSF electrodes 30 and 32 to clear the substance by applying direct current (DC) between extracranial and CSF electrodes 30 and 32. As used in the present application, including in the claims, direct current means a current having a constant polarity; the amplitude of the direct current may or may not vary over time, and may sometimes be zero.

For some applications, control circuitry 34 is activated to apply the direct current with an average amplitude of at least 1 mA, no more than 5 mA, and/or between 1 and 5 mA. Alternatively or additionally, for some applications, control circuitry 34 is activated to apply the direct current with an average amplitude of less than 1.2 V (such an amplitude may avoid electrolysis in the vicinity of one or both of the electrodes).

For some applications, such as when the substance is amyloid beta, control circuitry 34 is activated to configure extracranial electrode 30 to be a cathode, and CSF electrode 32 to be an anode. Alternatively, control circuitry 34 is activated to configure extracranial electrode 30 to be an anode, and CSF electrode 32 to be a cathode. For applications in which the voltage applied between the electrodes clears the substance electrophoretically, the selected polarity of the electrodes typically depends on whether the substance has a positive or negative effective charge. Similarly, for applications in which the voltage applied between the electrodes clears the substance electroosmotically, the selected polarity of the electrodes typically depends on whether the fluid has a positive or negative effective charge.

For some applications, control circuitry 34 is activated to apply the direct current as a series of pulses. For some applications, the series of pulses has an average pulse duration of at least 10 milliseconds, no more than 300 seconds, and/or between 10 milliseconds and 300 seconds, such as: (a) at least 10 milliseconds, no more than 100 milliseconds, and/or between 10 and 100 milliseconds, (b) at least 100 milliseconds, no more than 300 seconds (e.g., no more than 500 milliseconds), and/or between 100 and 300 seconds (e.g., between 100 and 500 seconds), (c) at least 500 milliseconds, no more than 5 seconds, and/or between 500 milliseconds and 5 seconds, (d) at least 5 seconds, no more than 10 seconds, and/or between 5 and 10 seconds, or (e) at least 10 seconds, no more than 100 seconds, and/or between 10 and 100 seconds. For some applications, the pulses are applied at a frequency of at least 0.001 Hz, no more than 1 kHz, and/or between 0.001 and 1 kHz, such as: (a) at least 100 Hz, no more than 1 kHz, and/or between 100 Hz and 1 kHz, (b) at least 20 Hz, no more than 100 Hz, and/or between 20 and 100 Hz, or (c) at least 1 Hz, no more than 10 Hz, and/or between 1 and 10 Hz. Alternatively or additionally, for some applications, the series of pulses has a duty cycle of at least 1%, no more than 50%, and/or between 1% and 50%, such as: (a) at least 1%, no more than 5%, and/or between 1% and 5%, (b) at least 5%, no more than 10%, and/or between 5% and 10%, (c) at least 10%, no more than 25%, and/or between 10% and 25%, or (d) at least 25%, no more than 50%, and/or between 25% and 50%. Typically, but not necessarily, the duty cycle is no more than 90%, because a given level of applied voltage produces higher current in the tissue if the capacitance in the tissue is allowed to discharge between pulses.

For some of the applications in which control circuitry 34 applies a voltage between extracranial and CSF electrodes 30 and 32 in a series of DC pulses, the resulting current decays because of the effects of tissue electrolytes. The current may decay by about two-thirds of its initial magnitude within tens of milliseconds after commencement of application of each pulse. In order to overcome this capacitance effect, control circuitry 34 is activated to apply the voltage intermittently, in order to provide time periods between pulses during which the capacitance discharges.

For some applications, control circuitry 34 is activated to apply the voltage intermittently with a preprogrammed frequency and/or duty cycle. These parameters may be (a) applicable to all patients or a subgroup of patients, (b) set during a calibration procedure upon placement of the electrodes, or (c) set based on a geometry of placement of extracranial and/or CSF electrodes 30 and/or 32. Alternatively, control circuitry 34 is configured to set these parameters in real time by sensing the current resulting from the applied voltage.

For some applications, control circuitry 34 is activated to measure the current resulting from the applied voltage during each of the applied pulses, and to terminate each of the applied pulses when the magnitude of the measured current falls below a threshold value. For example, the threshold value may be a preprogrammed constant, or may be based on (e.g., a percentage of) the initial current magnitude measured upon commencement of the respective pulse. Control circuitry 34 waits during a discharge period before applying the next pulse.

For some applications, control circuitry 34 is activated to apply, between extracranial and CSF electrodes 30 and 32, alternating current (AC) in:
  a primary subset of the pulses at a primary polarity selected to electrophoretically and/or electroosmotically clear the substance, at a primary voltage and with a primary average pulse duration, and
  a secondary subset of the pulses at a secondary polarity opposite the primary polarity, at a secondary voltage less than the primary voltage, and with a secondary average pulse duration greater than the primary average pulse duration.

Because of the lower secondary voltage, the secondary subset of the pulses to a large extent does not reverse the clearance of the substance achieved during application of the primary subset of the pulses. This technique may also help avoid electrolysis in the vicinity of one or both of the electrodes, even if the primary voltage is higher than a threshold DC voltage (e.g., 1.2 V) that might otherwise cause electrolysis.

For some applications, such as illustrated in FIG. 1C, the one or more extracranial electrodes 30 are placed such that one or more areas of build-up 64 of the substance in brain parenchyma 50 are between the one or more extracranial electrodes 30 and respective areas 80 of the CSF-filled space, such as ventricular system 54, nearest areas of build-up 64. For example, the area(s) of build-up 64 may include amyloid plaque and/or tau protein-related nerve tissue tangles. CSF electrode 32 may or may not be implanted near areas 80. For applications in which CSF electrode 32 is not implanted near areas 80, the substance of area of build-up 64 may still be driven into nearest areas 80 of the CSF-filled space, such as ventricular system 54, because nearest areas 80 are in fluid communication with CSF electrode 32 via CSF of the CSF-filled space, such as ventricular system 54, as discussed above. As mentioned above, a plurality of extracranial electrodes 30 may be placed, such as if there is more than one area of build-up 64 of the substance, or in general in order to provide good clearance of the substance.

Areas of build-up 64 may be identified, for example, by performing imaging of brain 52, such as MRI (e.g., functional MRI (fMRI)), PET imaging, or CT imaging of brain 52. For some applications, areas of build-up 64 are identified before placement of the one or more extracranial electrodes 30, and at least a first subset 82A (e.g., all) of the one or more extracranial electrodes 30 are located such that one or more respective areas of build-up 64 of the substance in brain parenchyma 50 are between the one or more extracranial electrodes 30 and respective areas 80 of the CSF-filled space. Optionally, a second subset 82B of the one or more extracranial electrodes 30 are located such that no areas of build-up 64 are between the one or more extracranial electrodes 30 and respective areas of the CSF-filled space. Typically, second subset 82B of the one or more extracranial electrodes 30 are used primarily to inhibit (e.g., prevent) formation of future build-up of the substance, and/or or in general in order to provide good clearance of the substance. First subset 82A may include a single one of or a plurality of extracranial electrodes 30, and second subset 82B may include a single one of or a plurality of extracranial electrodes 30. The first and second subsets 82A and 82B do not include any electrodes common to both subsets.

For other applications, areas of build-up 64 are identified after placement of the one or more extracranial electrodes 30, which may, for example, be placed at a number of locations around skull 40 (optionally in two-dimensional arrangement 70, described hereinbelow with reference to FIG. 2). For example, such identification may be performed soon after placement, and/or at period intervals after placement, such as every few months or years. A first subset 82A of the one or more extracranial electrodes 30 are identified as located such that one or more areas of build-up 64 of the substance in brain parenchyma 50 are between the one or more extracranial electrodes 30 and respective areas 80 of the CSF-filled space. Optionally, a second subset 82B of the one or more extracranial electrodes 30 are identified as located such that no areas of build-up 64 (or smaller areas than with respect to first subset 82A) are between the one or more extracranial electrodes 30 and respective areas of the CSF-filled space. First subset 82A may include a single one of or a plurality of extracranial electrodes 30, and second subset 82B may include a single one of or a plurality of extracranial electrodes 30. The first and second subsets 82A and 82B do not include any electrodes common to both sets.

Control circuitry 34 is activated to drive (a) first subset 82A of extracranial electrodes 30 and CSF electrode 32 to at least partially reduce (e.g., dissolve) the one or more respective areas of build-up 64 by clearing the substance, and (b) second subset 82B of the one or more extracranial electrodes 30 and CSF electrode 32 primarily to inhibit (e.g., prevent) formation of future build-up of the substance, and/or or in general in order to provide good clearance of the substance.

For some applications, control circuitry 34 is activatable (e.g., by configuring or programming) to drive a first average charge between the one or more extracranial electrodes 30 of first subset 82A and CSF electrode 32 over a 24-hour period of time, and a second average charge between the one or more extracranial electrodes 30 of second subset 82B and CSF electrode 32 over the 24-hour period of time. (The first average charge is not necessarily applied throughout the entire 24-hour period of time; similarly, the second average charge is not necessarily applied throughout the entire 24-hour period of time.) The first average charge is greater than the second average charge, such as at least 150, such at least 200%, e.g., at least 500% of the second average charge. (The ratio between the first and second average charges may be predetermined or adjustable, such as by programming the control circuitry.) The greater first average charge at least partially reduces (e.g., dissolves) the one or more respective areas of build-up 64 by clearing the substance, and the second average charge primarily inhibits (e.g., prevent) formation of future build-up of the substance. For example, the charges may be measured in coulombs. The difference in charges may be achieved, for example, by:

driving the one or more extracranial electrodes 30 of first subset 82A for a longer aggregate amount of time during the period of time than the one or more extracranial electrodes 30 of second subset 82B, such as at least as at least 1.5 times longer, e.g., at least 2 times longer, such as at least 5 times longer, applying a current between the one or more extracranial electrodes 30 of first subset 82A and CSF electrode 32 with a greater amperage than the current applied between the one or more extracranial electrodes 30 of second subset 82B and CSF electrode 32, such as at least 1.5 times greater, e.g., at least 2 times greater, such as at least 5 times greater, applying a voltage between the one or more extracranial electrodes 30 of first subset 82A and CSF electrode 32 with a greater voltage than the voltage applied between the one or more extracranial electrodes 30 of second subset 82B and CSF electrode 32, such as at least 1.5 times greater, e.g., at least 2 times greater, such as at least 5 times greater, and/or any combination of the above three parameters.

For some applications, control circuitry 34 is activated to drive extracranial and CSF electrodes 30 and 32 in sessions, each of which has a duration of several seconds or several minutes, or continuously for longer periods (e.g., 30 minutes). For some applications, the electrodes are not driven for a period that is at least an hour. Optionally, control circuitry 34 is activated to drive the electrodes only when the subject is sleeping, such as to take advantage of the widening of extracellular spaces and/or to inhibit any sensations that may be associated with the driving. For example, control circuitry 34 may be activated to use one or more of the electrodes as EEG electrodes to detect sleep. For some applications, power for activating and/or charging control circuitry 34 is transmitted from a wireless energy transmitter in a device applied to the head, such as a hat, or from a wireless energy transmitter in, under, or above a mattress, such as described hereinabove. For some applications, control circuitry 34 is activated to drive the electrodes according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the control circuitry does not drive the electrodes are provided in the pre-selected schedule.

For any of the applications described herein, CSF electrode 32 may be implanted in one of the following sites, rather than in ventricular system 54:
- a central canal of the spinal cord (which is in fluid communication with ventricular system 54); or
- a subarachnoid space (which is in fluid communication with ventricular system 54 because CSF drains into cisterns of the subarachnoid space via foramina of ventricular system 54).

For some applications, instead of implanting CSF electrode 32 in ventricular system 54, an electrode is implanted in a superior sagittal sinus.

Reference is again made to FIGS. 1A-C. For some applications, control circuitry 34 is configured to detect a voltage difference between parenchyma 50 and the CSF-filled space, and set a level of the voltage applied between extracranial and cerebrospinal fluid (CSF) electrodes 30 and 32 responsively to the detected voltage difference.

Figure 2:
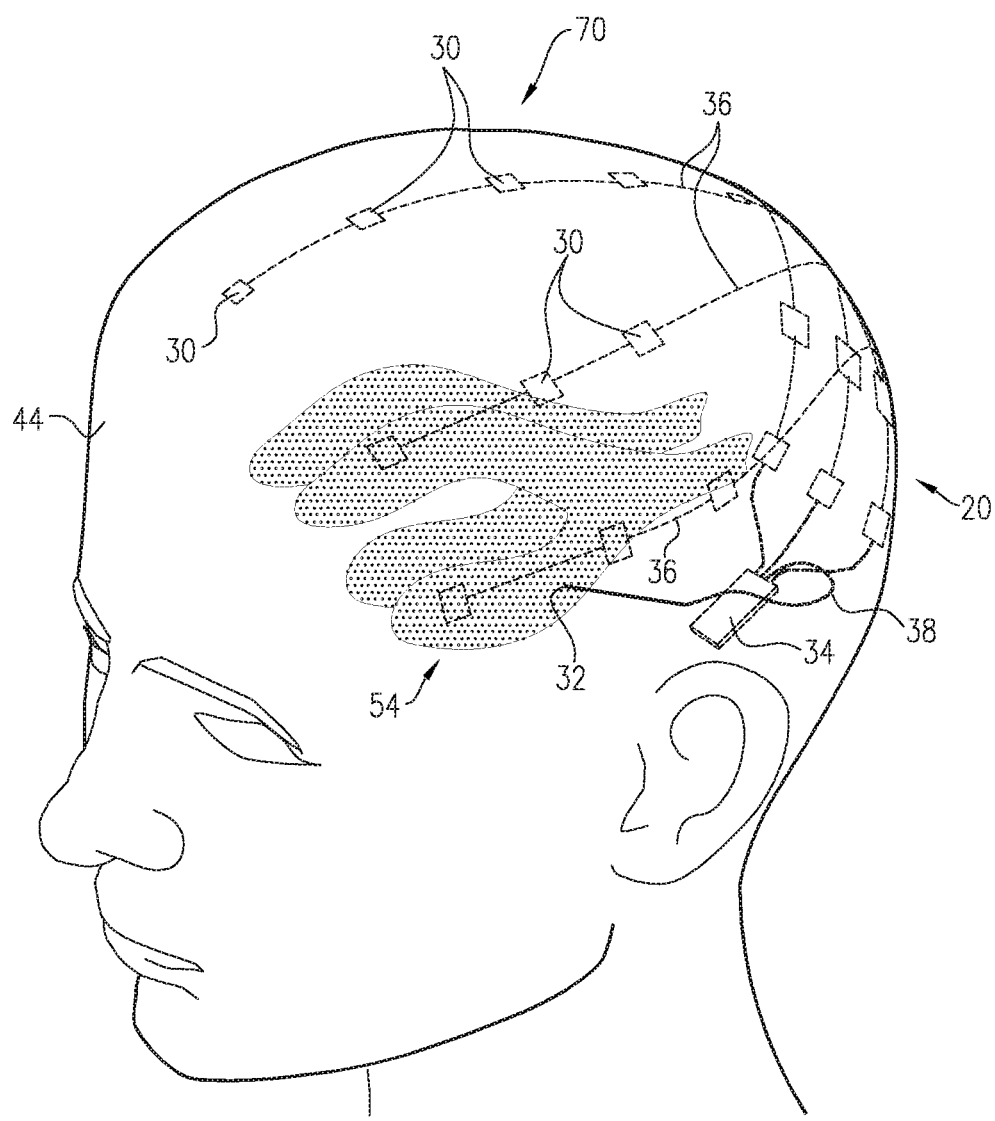
FIG. 2 is a schematic illustration of a configuration of the system of FIGS. 1A-C, in accordance with an application of the present invention.

Reference is now made to FIG. 2, which is a schematic illustration of a configuration of system 20, in accordance with an application of the present invention. In this configuration, system 20 comprises a plurality of extracranial electrodes 30, which are arranged as a two-dimensional arrangement 70 on skull 40, typically at a number of separate locations around the skull. Two-dimensional arrangement 70 may provide a good distribution of extracranial electrodes 30 around skull 40, in order to clear the substance from multiple locations within parenchyma 50.

For some applications, two-dimensional arrangement 70 comprises a two-dimensional array. Extracranial electrodes 30 are not necessarily evenly-spaced in the array in either dimension. For other applications, two-dimensional arrangement 70 is irregular, rather than organized as an array.

For some applications, two-dimensional arrangement 70 comprises at least a 2×3 arrangement of extracranial electrodes 30, such as at least a 3×3 arrangement, at least a 4×4 arrangement, or at least a 5×5 arrangement. (For clarity of illustration, FIG. 2 shows only three extracranial electrode leads 36 having three respective sets of extracranial electrodes 30 applied over the left hemisphere of the brain and the midline; optionally, additional extracranial electrode leads 36 and extracranial electrodes 30 are provided over the right hemisphere.)

Optionally, system 20 comprises a mesh of wires that helps define a shape of the electrode arrangement. Some or all of the wires may also serve as extracranial electrode leads 36.

Alternatively, extracranial electrodes 30 of system 20 are not arranged in a two-dimensional arrangement.

For some applications, system 20 is configured to, in addition to driving extracranial and CSF electrodes 30 and 32 to clear the substance from brain parenchyma 50 into the CSF-filled space, clear the substance from the CSF-filled space to superior sagittal sinus 142, such as using techniques described in PCT Publication WO 2017/072769 to Fostick et al. with reference to FIGS. 4A-G thereof, mutatis mutandis. For other applications, system 20 is not configured to clear the substance from the CSF-filled space to superior sagittal sinus 142.

PCT Publication WO 2017/072769 to Fostick et al., with reference to FIGS. 2A-B thereof, describe experimental results demonstrating that molecules of dye can be moved within rat brain tissue by applying a DC current using two electrodes implanted in the brain, and that in such a setup, a natural migration path is toward the ventricles. The inventors in the '769 PCT publication believe that application of the current between the electrodes may have moved the dye electrophoretically.

Additionally, the above-mentioned '769 PCT publication, with reference to FIG. 3 thereof, describes experimental results that demonstrate that soluble monomeric amyloid beta in its native conformation is negatively charged in artificial cerebrospinal fluid (aCSF) and is capable of moving in the electrical field without the need to add any amphiphilic detergents to provide the negative charge to the amyloid beta.

Yet additionally, experimental results described on p. 28, line 18-p. 29, line 13 of the above-mentioned '769 PCT publication demonstrate that electrophoretic movement of amyloid beta peptides is possible in the brain parenchyma with the electrical current-application protocol used in the experiment.

The inventors of the present application believe that the above-described experimental results in the '769 PCT publication provide evidence that the techniques described herein would be effective.

In an embodiment, techniques and apparatus described in one or more of the following applications, which are assigned to the assignee of the present application and are incorporated herein by reference, are combined with techniques and apparatus described herein:
- U.S. Pat. No. 9,731,122 to Gross;
- U.S. Pat. No. 9,616,221 to Gross;
- PCT Publication WO 2017/006327 to Gross;
- U.S. Pat. No. 9,724,515 to Fostick et al.;
- PCT Publication WO 2017/072769 to Fostick et al.;
- US Patent Application Publication 2018/0193646 to Fostick et al.;
- US Patent Application Publication 2018/0318575 to Gross et al.;
- U.S. patent application Ser. No. 16/353,407, filed Mar. 14, 2019, which published as US Patent Application Publication 2019/0282807; and
- International Patent Application PCT/IL2019/050284, filed Mar. 14, 2019, which published as PCT Publication WO 2019/175879.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   placing an extracranial electrode outside and in electrical contact with a skull of a subject identified as at risk of or suffering from a disease;
   implanting a cerebrospinal fluid (CSF) electrode in a ventricular system of a brain of the subject; and activating control circuitry to drive the extracranial and the CSF electrodes to clear a substance from brain parenchyma into the ventricular system of the brain.

2. The method according to claim 1, wherein the disease is Alzheimer's disease, and wherein placing the extracranial electrode comprises placing the extracranial electrode outside and in electrical contact with the skull of the subject identified as at risk of or suffering from Alzheimer's disease.

3. The method according to claim 1, wherein the substance includes amyloid beta, and wherein activating the control circuitry comprises activating the control circuitry to drive the extracranial and the CSF electrodes to clear the amyloid beta from the brain parenchyma into the ventricular system of the brain.

4. The method according to claim 1,
wherein placing the extracranial electrode comprises placing a plurality of extracranial electrodes, and
wherein the method further comprises, after placing the plurality of extracranial electrodes:
identifying one or more areas of build-up of the substance in the parenchyma between the extracranial electrodes and respective areas of the ventricular system of the brain nearest the areas of build-up; and
identifying a first subset of the one or more extracranial electrodes as located such that one or more of the areas of build-up of the substance in brain parenchyma are between the one or more extracranial electrodes and the respective areas of the ventricular system.

5. The method according to claim 4, wherein activating the control circuitry to clear the substance from the brain parenchyma comprises activating the control circuitry to drive a first average charge between the one or more extracranial electrodes of the first subset and the CSF electrode over a 24-hour period of time, and a second average charge between (a) the one or more extracranial electrodes of a second subset of the one or more extracranial electrodes and (b) the CSF electrode over the 24-hour period of time, the first average charge greater than the second average charge, and the first and the second subsets not including any extracranial electrodes common to both subsets.

6. The method according to claim 4, wherein identifying the one or more areas of build-up comprises performing imaging of the brain.

7. The method according to claim 1, wherein activating the control circuitry to drive the extracranial and the CSF electrodes comprises activating the control circuitry to drive the extracranial and the CSF electrodes to clear the substance by applying a non-excitatory current between the extracranial and the CSF electrodes.

8. The method according to claim 1, wherein activating the control circuitry to drive the extracranial and the CSF electrodes comprises activating the control circuitry to drive the extracranial and the CSF electrodes to clear the substance by applying direct current between the extracranial and the CSF electrodes with an average amplitude of between 1 and 5 mA.

9. The method according to claim 1, wherein activating the control circuitry to drive the extracranial and the CSF electrodes comprises activating the control circuitry to drive the extracranial and the CSF electrodes to clear the substance by applying direct current between the extracranial and the CSF electrodes with an average amplitude of less than 1.2 V.

10. The method according to claim 1, wherein activating the control circuitry to drive the extracranial and the CSF electrodes comprises activating the control circuitry to drive the extracranial and the CSF electrodes to clear the substance by applying direct current between the extracranial and the CSF electrodes as a series of pulses.

11. A method comprising:
placing a two-dimensional arrangement of extracranial electrodes outside and in electrical contact with a skull of a subject identified as at risk of or suffering from a disease;
implanting a cerebrospinal fluid (CSF) electrode in a ventricular system of a brain of the subject; and
activating control circuitry to drive the extracranial and the CSF electrodes to clear a substance from brain parenchyma into at least one region of the brain selected from the group consisting of: a subarachnoid space of the brain and dural sinuses of the brain.

12. The method according to claim 11, wherein the disease is Alzheimer's disease, and wherein placing the two-dimensional arrangement of extracranial electrodes comprises placing the two-dimensional arrangement of extracranial electrodes outside and in electrical contact with the skull of the subject identified as at risk of or suffering from Alzheimer's disease.

13. The method according to claim 11, wherein the substance includes amyloid beta, and wherein activating the control circuitry comprises activating the control circuitry to drive the extracranial and the CSF electrodes to clear the amyloid beta from the brain parenchyma into the at least one region of the brain.

14. The method according to claim 11, further comprising, after placing the two-dimensional arrangement of extracranial electrodes:
identifying one or more areas of build-up of the substance in the parenchyma between the two-dimensional arrangement of extracranial electrodes and respective areas of the ventricular system of the brain nearest the areas of build-up; and
identifying a first subset of the one or more extracranial electrodes as located such that one or more of the areas of build-up of the substance in brain parenchyma are between the one or more extracranial electrodes and the respective areas of the ventricular system.

15. The method according to claim 14, wherein activating the control circuitry to clear the substance from the brain parenchyma comprises activating the control circuitry to drive a first average charge between the one or more extracranial electrodes of the first subset and the CSF electrode over a 24-hour period of time, and a second average charge between (a) one or more extracranial electrodes of a second subset of the one or more extracranial electrodes and (b) the CSF electrode over the 24-hour period of time, the first average charge greater than the second average charge, and the first and the second subsets not including any extracranial electrodes common to both subsets.

16. The method according to claim 14, wherein activating the control circuitry to drive the extracranial and the CSF electrodes comprises activating the control circuitry to drive the extracranial and the CSF electrodes to clear the substance by applying a non-excitatory current between the extracranial and the CSF electrodes.

17. The method according to claim 14, wherein activating the control circuitry to drive the extracranial and the CSF electrodes comprises activating the control circuitry to drive the extracranial and the CSF electrodes to clear the substance by applying direct current between the extracranial and the CSF electrodes with an average amplitude of between 1 and 5 mA.

18. The method according to claim 14, wherein activating the control circuitry to drive the extracranial and the CSF electrodes comprises activating the control circuitry to drive the extracranial and the CSF electrodes to clear the substance by applying direct current between the extracranial and the CSF electrodes with an average amplitude of less than 1.2 V.

19. The method according to claim 14, wherein activating the control circuitry to drive the extracranial and the CSF electrodes comprises activating the control circuitry to drive the extracranial and the CSF electrodes to clear the substance by applying direct current between the extracranial and the CSF electrodes as a series of pulses.

* * * * *